United States Patent [19]

Schenke et al.

[11] Patent Number: 5,532,364

[45] Date of Patent: Jul. 2, 1996

[54] ENANTIOMERICALLY PURE 2-OXA-5,8-DIAZABICYCLO[4.3.0]NONANES AND PROCESS FOR THEIR PREPARATION

[75] Inventors: Thomas Schenke, Bergisch Gladbach; Andreas Krebs, Odenthal; Uwe Petersen, Leverkusen, all of Germany

[73] Assignee: Bayer Aktiengesellschaft, Leverkusen, Germany

[21] Appl. No.: 292,643

[22] Filed: Aug. 18, 1994

Related U.S. Application Data

[62] Division of Ser. No. 998,284, Dec. 30, 1992, Pat. No. 5,436,334.

[30] Foreign Application Priority Data

Jan. 10, 1992 [DE] Germany .......................... 42 00 415.2

[51] Int. Cl.$^6$ ................................................ C07D 498/04
[52] U.S. Cl. .................................................... 544/105
[58] Field of Search ............................................ 544/105

[56] References Cited

U.S. PATENT DOCUMENTS

| | | | |
|---|---|---|---|
| 4,634,775 | 1/1987 | Beck et al. | 548/402 |
| 4,990,517 | 2/1991 | Petersen et al. | 514/300 |

FOREIGN PATENT DOCUMENTS 0350733  1/1990  European Pat. Off. .

OTHER PUBLICATIONS

Patai, The Chemistry of the ether linkage Interscience, 1967, G. Kohnstam and D. K. H. Williams, pp. 118–120.
Patai, The Chemistry of the Sulphonium group Interscience, 1981, D. C. Dittmer & B. H. Patwardham, pp. 394–395.
Gundermann Angew. Chem. Internat. Edit., vol. 2, 1963, No. 11, pp. 674–683.
Thioethers; Differences and Analogies w/ Ethers, pp. 591–594 L. Brandsma & J. F. Arens.
P. Ruth et al., "Primary Structure . . . Skeletal Muscle", *Reports*, 8 Sep. 1989, pp. 1115–1118.
T. Tanabe et al., "Primary Structure of the Receptor . . . Muscle", *Nature*, vol. 328, 23 Jul. 1987, pp. 313–318.
Tsien et al., 1988, Trends in Neurol. Sci., 11:431–438.
Singer et al., 1991, Science 253:1553–1557.
Rosario et al., 1989, Neurosci. 29, 735–747.
Carbone et al., 1990, Pflugers Arch., 416:170–179.
Zernig et al., 1986, Eur. J. Pharmacol. 128, 221–229.
Gluzman, 1981, Cell 23:175.
Chen et al., 1987, Mol. Cell. Biol. 7:2745–2752.
Messing et al., 1985, J. Pharmacology and Exp. Therapeutics 235:407–411.
Chem. Pharm. Bull. 17(5) 980–086 (1969); Syntheses of 3,4–Epoxy– and 3,4–Epimino–pyrrolidines), Oida et al.
Zh. Org. Khim. 3, 1509 (1967); Synthesis of Pyrrolidine, Pyrroline, and Pyrrole Derivatives Based on Sulfur Arysulfonylmonoimino Dioxides, Levchenko et al.
J. Chem. Research (S), 1989, 224–225; Applications of Phase Transfer Catalysis. Part 47. Relative Stabilities and Performances of Various Phase Transfer Catalysts, Dehmlow et al.
Lacerda et al., 1991, Nature 352:527.
Veradi et al., 1991, Nature 352:159.
Ruth et al., 1989, Science 245:1115.
Academic Press, 1978, pp. 217–220; Phase Transfer Catalysis, Starks.
Angew. Chem 92, 14–25 (1980); Chromatographische Racemattrennung, Blaschke.
Yool and Schwarz, 1991, Nature 349: 700–704.
P. A. Powers et al., "Skeletal Muscle . . . Single Gene", *The Journal of Biological Chemistry*, vol. 267, No. 32, 15 Nov. 1992, pp. 22967–22972.
H. Perst, Oxanium Ions in Organic Chemistry Weinheim, 1971, p. 101.
Conant, The Chemistry of Organic Compounds, 5th Ed. (1959), p. 333.

*Primary Examiner*—Philip I. Datlow
*Attorney, Agent, or Firm*—Sprung Horn Kramer & Woods

[57] ABSTRACT

This invention relates to a process for preparing an enantiomerically pure compound of the formula

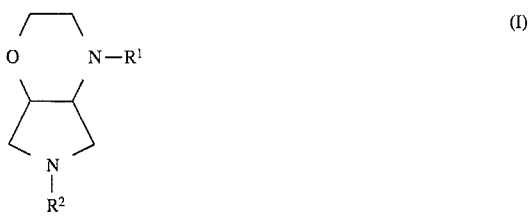

(I)

wherein $R^1$ and $R^2$ are defined herein starting with a S,S- or R,R-dihydropyridine derivative of the formula

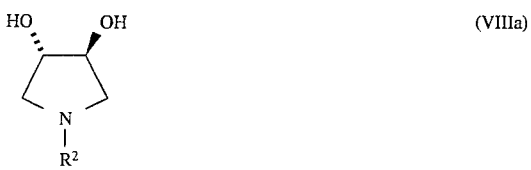

(VIIIa)

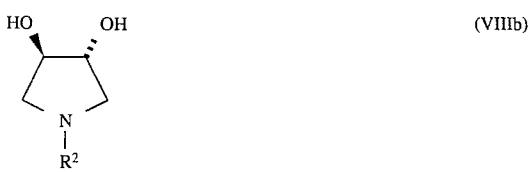

(VIIIb)

2 Claims, No Drawings

ENANTIOMERICALLY PURE 2-OXA-5,8-DIAZABICYCLO[4.3.0]NONANES AND PROCESS FOR THEIR PREPARATION

This application is a divisional, of application Ser. No. 07/998,284, filed Dec. 30, 1992 now U.S. Pat. No. 5,436,334.

The invention relates to enantiomerically pure 2-oxa-5,8-diazabicyclo[4.3.0]nonanes and processes for their preparation.

EP 350 733 and JA 3188-080 have already disclosed trans- 2-oxa-5,8-diazabicyclo[4.3.0]nonanes which are interesting intermediates for antibacterially highly effective compounds. 2-Oxa-5,8-diazabicyclo[4.3.0]nonane has two chiral carbon atoms and can therefore occur in four stereoisomeric forms. Since, in the case of biologically active compounds, the properties of one enantiomer can be quite different from those of the other stereoisomers, it is desirable to provide the enantiomerically pure active compounds.

The present invention therefore describes processes for the preparation of enantiomerically pure compounds of the formula (I),

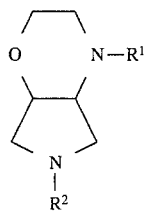
(I)

where $R^1$ represents H, $C_1$–$C_3$-alkyl, phenyl, benzyl, 1-phenylethyl, $C_1$–$C_3$-alkanoyl, $C_1$–$C_4$-alkoxycarbonyl, preferably H, methyl, benzyl, 1-phenylethyl, acetyl, ethoxycarbonyl and t-butoxycarbonyl, particularly preferably H, methyl, benzyl and 1-phenylethyl
and $R^2$ represents H, benzyl, $C_1$–$C_5$-alkanoyl, benzoyl which is optionally mono- or disubstituted by halogen or $C_1$–$C_4$-alkyl, $C_1$–$C_4$-alkoxycarbonyl, methanesulphonyl, benzenesulphonyl and toluenesulphonyl, preferably H, benzyl, acetyl, benzoyl, ethoxycarbonyl, t-butoxycarbonyl, methanesulphonyl and p-toluenesulphonyl, particularly preferably H, benzyl, t-butoxycarbonyl, benzoyl and p-toluenesulphonyl.

It has now been found that compounds of the formula (I) with the cis configuration are obtained by converting 2,5-dihydropyrrole derivatives of the formula (II)

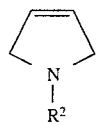
(II)

in which $R^2$ has the abovementioned meaning, but cannot be hydrogen, by reaction with N-bromosuccinimide or bromine in ethylene glycol, into racemic intermediates of the formula (IIIa)

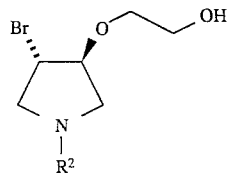
(IIIa)

in which $R^2$ has the abovementioned meaning, but cannot be hydrogen, and by converting this into a compound of the formula (IIIb)

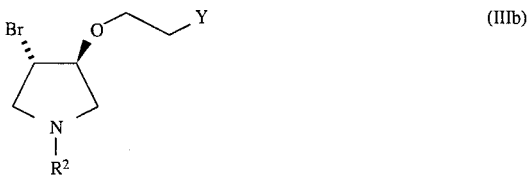
(IIIb)

in which $R^2$ has the abovementioned meaning, but cannot be hydrogen, and Y represents Cl, Br or O—$SO_2$—$R^3$, where $R^3$ denotes methyl, phenyl or methylphenyl, which compound is cyclised by reacting with an amine of the formula (IV)

$$R^4-NH_2 \qquad (IV)$$

in which $R^4$ represents hydrogen, $C_1$–$C_3$-alkyl, phenyl, benzyl or 1-phenylethyl, to give a racemic compound of the formula (V)

(V)

in which $R^2$ and $R^4$ have the abovementioned meanings, and a radical $R^4$ optionally present as a protective group is then cleaved off and, by alkylation or acylation, replaced by a radical $R^1$.

Compounds of the formula (IIIb) in which Y can represent Cl or Br can also be obtained by reacting a compound of the formula (II)

(II)

in which $R^2$ has the abovementioned meaning, but cannot be hydrogen, with N-bromosuccinimide or bromine in the presence of a compound of the formula (VI)

$$HO\frown Y \qquad (VI)$$

in which Y represents Cl or Br.

Compounds of the formula (IIIb) in which Y represents Br can also be obtained by reacting a compound of the formula (II)

(II)

in which $R^2$ has the abovementioned meaning, but cannot be hydrogen, with bromine in the presence of ethylene oxide.

It has also been found that enantiomerically pure compounds of the formulae (Ia)–(Id)

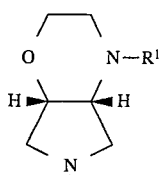 (Ia)

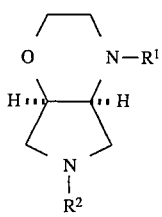 (Ib)

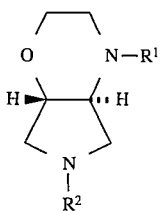 (Ic)

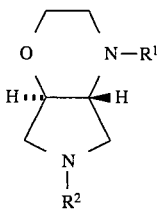 (Id)

are obtained by converting a racemic cis or trans compound of the formula (I),

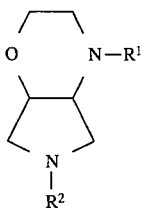 (I)

in which $R^1$ and $R^2$ have the abovementioned meaning and in which at least one of the two nitrogen atoms must have basic properties, into a mixture of the diastereomeric salts using an enantiomerically pure acid, separating said mixture into the enantiomerically pure salts by crystallisation, and subsequently liberating the enantiomerically pure bases therefrom with the aid of a base.

Enantiomerically pure compounds of the formula (Ia) or (Ib)

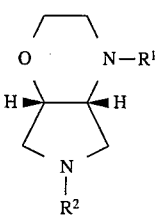 (Ia)

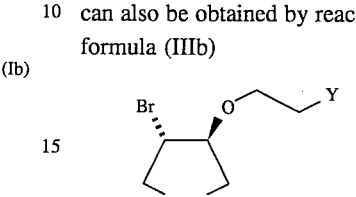 (Ib)

can also be obtained by reacting racemic compounds of the formula (IIIb)

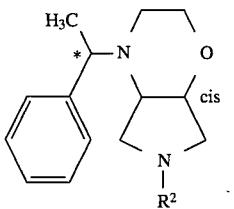 (IIIb)

with enantiomerically pure R- or S-1-phenylethylamine to give a mixture of, in each case, two diastereomeric compounds of the formula (VII),

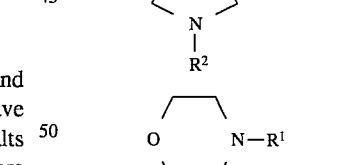 (VII)

in which $R^2$ has the abovementioned meaning, and separating the mixture into enantiomerically pure compounds, cleaving off the phenylethyl radical by hydrogenolysis if required, and optionally replacing it by a radical $R^1$.

Enantiomerically pure compounds of the formulae (Ia) and (Ib)

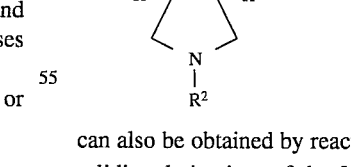 (Ia)

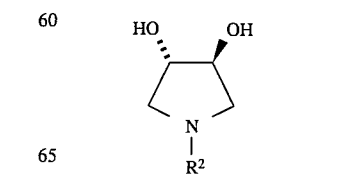 (Ib)

can also be obtained by reacting S,S- or R,R-dihydroxypyrrolidine derivatives of the formula (VIIIa) or (VIIIb)

 (VIIIa)

-continued

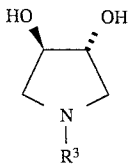
(VIIIb)

in which $R^2$ has the abovementioned meaning, but cannot be hydrogen, with allyl bromide or allyl chloride in the presence of a base to give compounds of the formula (IXa) or (IXb) respectively

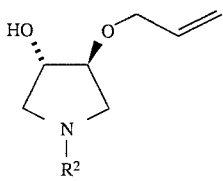
(IXa)

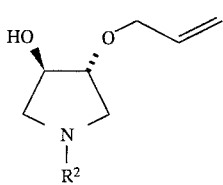
(IXb)

which are broken down, by ozonolysis and subsequent reduction, into compounds of the formula (Xa) and (Xb) respectively

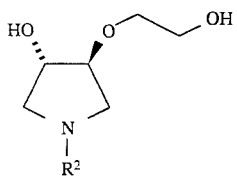
(Xa)

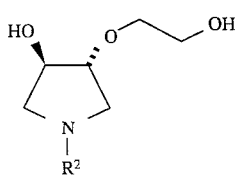
(Xb)

which, by acylation with sulphonyl chlorides $R^3$—$SO_2Cl$, are reacted to give sulphonic acid esters of the formula (XIa) and (XIb) respectively, $R^3$ having the abovementioned meaning,

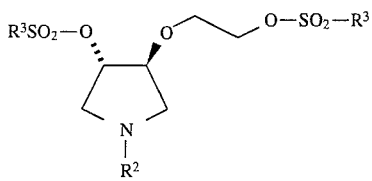
(XIa)

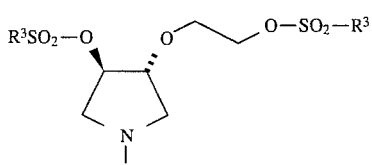
(XIb)

which, by reacting with amines of the formula (IV), $R^4$—$NH_2$ (IV)

in which $R^4$ has the abovementioned meaning, are cyclised to give compounds of the formula (XIIa) and (XIIb) respectively

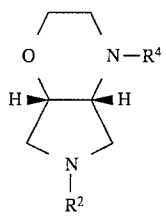
(XIIa)

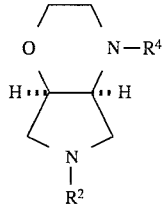
(XIIb)

in which the radical $R^4$ optionally serving as a protective group is cleaved off and optionally replaced, by acylation or alkylation, by a radical $R^1$.

In the following, the individual steps of the process according to the invention are described in more detail.

In the first step of the process according to the invention, acylated or sulphonylated 2,5-dihydropyrrole derivatives of the formula (II) are converted into racemic intermediates of the formula (III), $R^2$ having the abovementioned meaning with the exception of H.

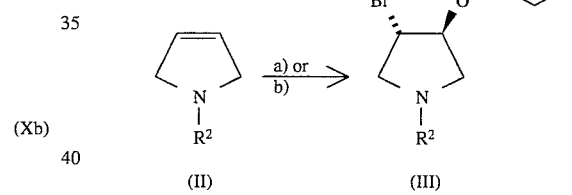

(II)  (III)

a) N-bromosuccinimide,

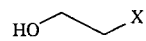

b) $Br_2$, ethylene oxide
X=OH, Cl, Br
Y=OH, Cl, Br, $OSO_2R^3$ with $R^3$=methyl, phenyl, 4-methylphenyl.

In this instance, compounds of the formula (III) in which Y represents OH are converted by generally known methods into a sulphonic acid ester, for example with methanesulphonyl chloride or p-toluenesulphonyl chloride in the presence of an auxiliary base such as pyridine, triethylamine or sodium hydroxide solution.

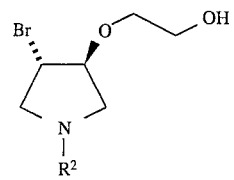

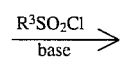

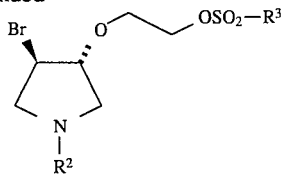

The 1-acylated or 1-sulphonylated 2,4-dihydropyrroles of the formula (II) required as starting materials are known from the literature and can be obtained by acylation of 2,5-dihydropyrroles (Chem. Pharm. Bull. 17, 980 (1969)) or by elimination of hydrogen bromide from 1-sulphonylated 3-bromo-tetrahydropyrroles (Zh. Org. Khim. 3, 1509 (1967)).

The compounds of the formula (II) can also be obtained, according to a novel process, by reacting carboxamides or sulphonamides with cis-1,4-dichloro-2-butene or cis-1,4-dibromo-2-butene and alkali metal hydroxides and/or carbonates using phase transfer catalysis. Aliphatic and aromatic carboxamides or sulphonamides can be used as amides, such as for example: isobutyramide, butyramide, pivalamide, phenylacetamide, benzamide, 2-chloro-benzamide, 4-chloro-benzamide, 2,6-difluoro-benzamide, 4-tert-butyl-benzamide, 4-methyl-benzenesulphonamide, methanesulphonamide.

The acid acceptors used can be alkali metal hydroxides and carbonates or mixtures of these, both as the solid or in the form of their aqueous solutions.

The phase transfer catalysts used can be selected from all of the compounds commonly used for this catalysis (see, e.g. J. Chem. Research (S), 1989, 224 and C. M. Starks, "Phase transfer catalysis", Academic Press, New York, 1978). The diluents used can be selected from all the solvents which are inert or nearly inert with respect to the reactants and to the acid acceptor, such as, for example, aliphatic and aromatic hydrocarbons, halogenated aromatic compounds and ethers.

The conversion of (II) to (III) by the process according to the invention can be carried out with or without an additional solvent. Suitable solvents are all inert solvents. Among those which may be used are hydrocarbons such as benzene, toluene or xylenes, ethers such as dioxane, tetrahydrofuran or t-butyl methyl ether, dipolar aprotic solvents such as dimethylformamide, dimethyl sulphoxide or N-methylpyrrolidone or chlorinated hydrocarbons such as methylene chloride, chloroform or chlorobenzene. When no additional solvent is present, the ethanol derivative used is employed in up to twenty-fold excess. The reaction temperature can be varied over a wide range. Temperatures of −20° C. to +50° C., preferably between 0° C. and +30° C., are used.

In the second step of the process according to the invention, the compounds of the formula (III) are cyclised with ammonia or a primary amine (IV) to give the 2-oxa-5,8-diazabicyclo[4.3.0]nonane derivatives (V). In this process, $S_N2$-substitution of the bromine atom leads to formation of the cis configuration

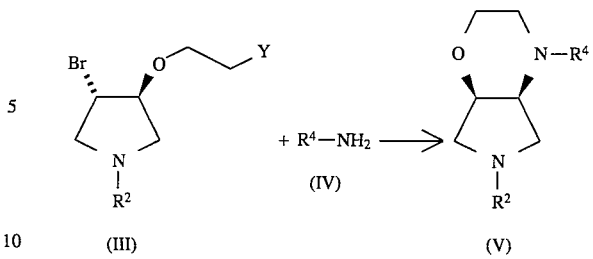

$R^4$=H, $C_1$–$C_3$-alkyl, phenyl, benzyl, (rac, R- or S-)-1-phenylethyl.

The conversion of (III) to (V) by the process according to the invention is carried out in a solvent. Hydrocarbons such as benzene, toluene, xylenes or tetralin, ethers such as dioxane, dibutyl ether, diethylene glycol dimethyl ether, alcohols such as butanol and glycol monomethyl ether, and dipolar aprotic solvents such as dimethyl sulphoxide and N-methylpyrrolidone can be used. Xylenes and tetralin are preferred.

The reaction temperature can be varied over a fairly wide range. In general, the conversions are carried out between 80° C. and 210° C., preferably between 110° C. and 160° C.

To achieve higher reaction temperatures when low-boiling solvents or volatile amines $R^4$—$NH_2$ are used, the reaction can be carried out under pressure. Pressures of 0.5 bar to 200 bar, preferably 1 bar to 100 bar, can be used.

In order to bind the hydrogen halides and sulphonic acids liberated during the reaction, auxiliary bases are added. Suitable for this purpose are alkali metal carbonates or alkali metal hydrogen carbonates, as well as an excess of the amine $R^4$—$NH_2$ used or other a mines and amidines such as triethylamine, 1,4-diazabicyclo[2.2.2]octane (Dabco), diazabicyclo[4.3.0]nonene (DBN) or diazabicyclo[6.3.0]undecene (DBU).

In a further step of the process according to the invention, the substituents $R^2$ and $R^4$ of the bicyclics (V), if they function as protective groups, can optionally be cleaved off. Acyl radicals are removed by hydrolysis. Strong acids or strong bases are suitable for the hydrolysis. Hydrochloric acid or alkali metal hydroxides or alkaline earth metal hydroxides are preferably used.

Benzyl radicals and 1-phenylethyl radicals are removed by hydrogenolysis. The catalyst used is palladium, both as a sponge and on carriers such as activated carbon, calcium carbonate or barium sulphate, and palladium hydroxide on activated carbon.

Sulphonic acid residues are cleaved off by reduction with sodium in liquid ammonia or butanol, with sodium naphthalide, or under acid conditions with hydrogen bromide.

The nitrogen groups which are free due to the cleaving off of protective groups can be acylated again if required, so that compounds of the formula (V) can yield compounds corresponding to the scope of the formula (I).

The process according to the invention further comprises the resolution of the racemic compounds of the structure (I) into the optical antipodes. These racemate resolutions can be carried out by the following processes:

1) The racemic compounds of the formula (I) can, if they have basic properties, be reacted with enantiomerically pure acids, e.g. carboxylic acids or sulphonic acids such as N-acetyl-L-glutamic acid, N-benzoyl-L-alanine, 3-bromo-camphor-9-sulphonic acid, camphor-3-carboxylic acid, cis-camphoric acid, camphor-10-sulphonic acid, O,O'-dibenzoyl-tartaric acid, D- or L-tartaric acid, mandelic acid, α-methoxy-phenylacetic acid, 1-phenyl-ethanesulphonic acid, α-phenyl-succinic acid to give a mixture of the diastereomeric salts which may be separated by fractionated crystallisation into the enantiomerically pure salts (see P. Newmann, Optical Resolution Procedures for Chemical Compounds, Volume 1). By treating these salts with alkali metal hydroxides or alkaline earth metal hydroxides, the enantiomerically pure amines can be liberated.

The following set of equations illustrates as an example of a racemate resolution the separation of cis-5-benzyl-2-oxa-5,8-diazabicyclo[4.3.0]nonane via the tartrates and the subsequent conversion into the enantiomerically pure cis-2-oxa-5,8-diazabicyclo[4.3.0]nonanes:

2) Both the racemic amines of the formula (I) and the racemic intermediates of the formula (III) can, after acylation if appropriate, be resolved chromatographically on chiral support materials (cf., e.g. G. Blaschke, Angew. Chem. 92, 14 [1980]).

3) Both the racemic amines of the formula (I) and the racemic intermediate products of the formula (III) may be converted, by chemical linking with chiral acyl radicals, into diastereomeric mixtures which can be resolved, by distillation, crystallisation or chromatography, into the enantiomerically pure acyl derivatives from which the enantiomerically pure amines can be isolated by hydrolysis. Examples

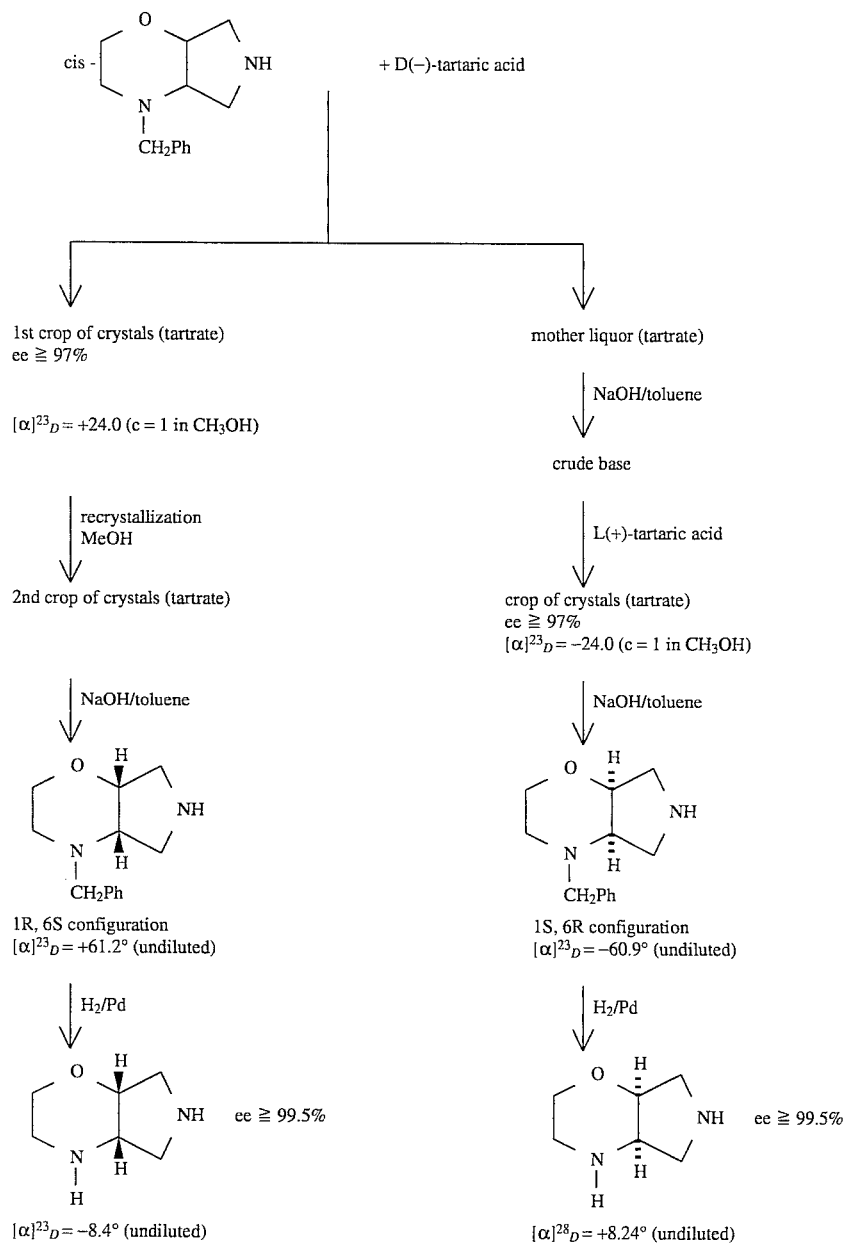

Racemic trans-8-benzyl-2-oxa-5,8-diazabicyclo[4.3.0]nonane may be resolved in an analagous manner, using D- or L-tartaric acid, into the corresponding enantiomerically pure compounds and be converted, by cleaving off the benzyl group, into 1R,6R-2-oxa-5,8-diazabicyclo[4.3.0] nonane and 1S,6S- 2-oxa-5,8-diazabicyclo[4.3.0]nonane.

of reagents for linking with chiral acyl radicals are: α-methoxy-α-trifluoromethyl-phenylacetyl chloride, menthyl isocyanate, D- or L-α-phenylethylisocyanate, menthyl chloroformate, camphor-10-sulphonyl chloride.

4) In the course of the synthesis of the compounds of the formula (I), chiral rather than achiral protective groups may be introduced. In this way, diastereomers which can be separated are obtained. For example, the amine component used for the cyclisation (III)→(V) may comprise the enantiomerically pure 1-phenylethylamines, as shown in the following diagram.

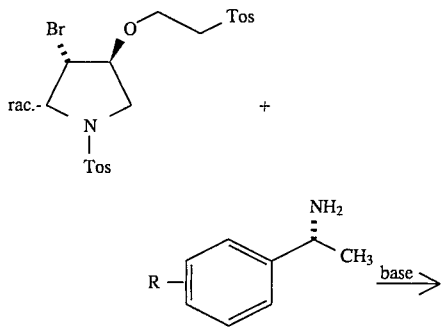

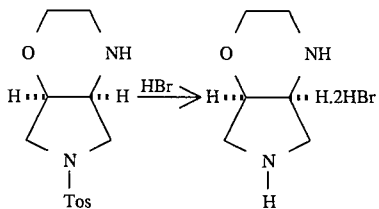

The process according to the invention, however, also comprises the preparation of enantiomerically pure compounds of the formula (I) from enantiomerically pure starting materials or using chiral auxiliaries and catalysts. As an illustration, the synthesis of 1S,6R-2-oxa-5,8-diazabicyclo [4.3.0]nonane starting from S,S-3,4-dihydroxypyrrolidine derivatives (German Offenlegungsschrift 3 403 194 of which U.S. Pat. No. 4,634,775 is an English language counterpart thereof) which are known from the literature, is shown:

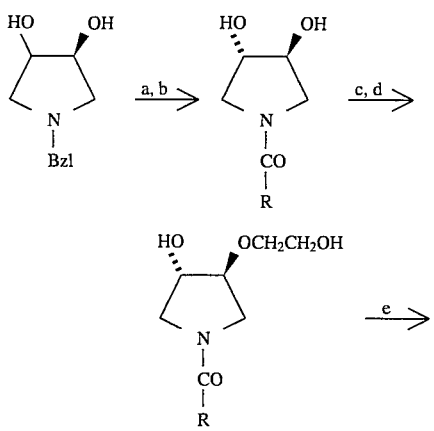

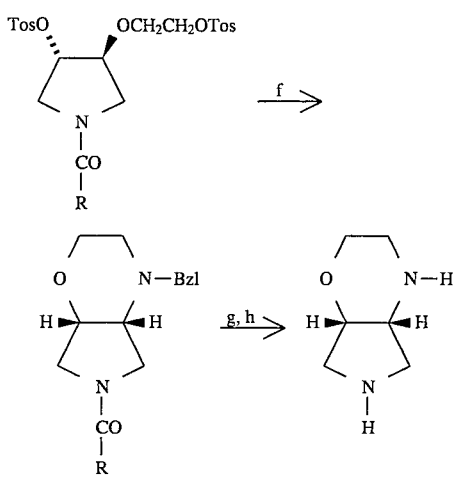

R = for example, (CH$_3$)$_3$C—O
a: H$_2$, Pd/active carbon
b: acylation
c: NaH, BrCH$_2$COOC$_2$H$_5$ or  c: CH$_2$=CH—CH$_2$Br, NaH
d: LiBH$_4$  d: O$_3$, NaBH$_4$,
e: tosyl chloride, NEt$_3$,
f: benzylamine, xylene, reflux
g: hydrolysis
h: H$_2$, Pd/active carbon The compounds according to the invention constitute valuable intermediate compounds for novel quinolonecarboxylic acids and naphthyridonecarboxylic acids which are the subject-matter of an application of the same date.

These novel quinolonecarboxylic acid and naphthyridonecarboxylic acid compounds are notable for good tolerability and high antibacterial activity which is particularly pronounced with regard to Gram-positive organisms.

The following table demonstrates the advantage of the compound from Reference Example 2, compared to ciprofloxacin in the model of the mouse infected with *Staph. aureus*:

TABLE

| Activity in the infection by *Staph. aureus* in the mouse (mg/kg) | | |
|---|---|---|
| Substance | p.o. | s.c. |
| Ciprofloxacin | 80 | 80 |
| Reference Example 2 | 10 | 10 |

The following examples illustrate the invention.

EXAMPLE 1

1-Benzoyl-2,5-dihydro-pyrrole 121 g (1 mol) of benzamide in 3 l of toluene are introduced initially, 200 g of powdered potassium hydroxide are introduced with stirring, 32 g (0.1 mol) of tetrabutylammonium bromide are added and the mixture is heated to 40° C. 243 g (1 mol) of 88% cis-1,4-dibromo-2-butene are then added dropwise in such a way that the internal temperature does not exceed 60° C. The mixture is stirred for another 5 hours at 50° C., then poured into water, and the organic phase is separated off, washed with water, dried and concentrated. The residue is distilled under reduced pressure.

Yield: 130 g (75% of theory) Content: 98%, determined by gas chromatography Boiling point: 98° to 104° C./0.2 mbar.

EXAMPLE 2

2,5-Dihydro-1-(4-methyl-phenyl-sulphonyl)-pyrrole

A 1.0 l stirred vessel having a bottom discharge valve is charged with 51.3 g (0.3 mol) of p-toluenesulphonamide, 200 ml (1.2 mol) of 6N sodium hydroxide, 400 ml of toluene and 4.44 g (15 mmol) of tetrabutyl-ammonium chloride and, at an internal temperature of 60° C., 37.5 g (0.3 mol) of cis-1,4-dichloro-2-butene are added dropwise with vigorous stirring over a period of 20 minutes, whereupon the internal temperature rises by 2° C. The mixture is stirred for another hour at 60° C. and another 2 hours at 80° C., the aqueous phase is then separated off and the organic phase is washed at 60° C. with 100 ml of 1N sulphuric acid and 2×200 ml of water. The organic phase is filtered through a fluted filter moistened with toluene into a crystallisation vessel. Upon cooling to 0° C., 44.8 g of product, melting point 128° to 130° C., are obtained. From the concentrated mother liquor (approx. 20 g), recrystallisation from 100 ml of isopropanol or 60 ml of toluene affords a further 12 to 15 g of product, melting point: 125° to 127° C. Yield: 85 to 90% of theory.

EXAMPLE 3 cis-5-Benzyl-2-oxa-5,8-diazabicyclo[4.3.0]nonane a) trans-1-benzoyl-3-bromo-4-(2-hydroxyethoxy)pyrrolidine

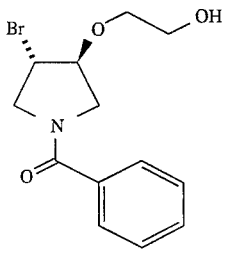

95 g (0.55 mol) of 1-benzoyl-3-pyrroline are dissolved in 380 g of ethylene glycol, and 101 g (0.57 mol) of N-bromosuccinimide are added in 5 g portions over a period of 2 hours at room temperature. The mixture is then stirred overnight at room temperature and poured into water, followed by extraction with methylene chloride, drying over magnesium sulphate and concentration of the solution. The residue (188 g) was chromatographed with ethyl acetate on silica gel.

Yield: 136.5 g (78% of theory), Content according to GC: 99%.

b) trans-3-bromo-4-(2-hydroxyethoxy)-1-tosylpyrrolidine

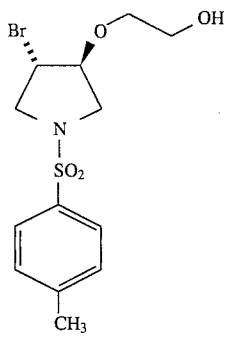

According to the same procedure as in Example 3a), 1-tosyl-3-pyrroline is reacted.

Yield: 97.6% of theory, Melting point: 77° C. (from diisopropyl ether).

c) trans-1-benzoyl-3-bromo-4-(2-tosyloxyethoxy)-pyrrolidine

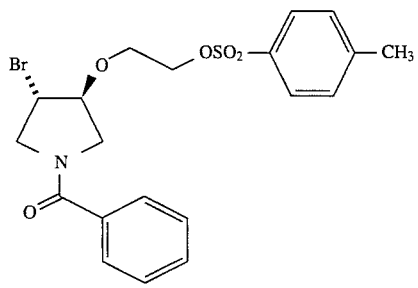

92 g (0.239 mol) of trans-1-benzoyl-3-bromo-4-(2-hydroxyethoxy)-pyrrolidine, 32 g (0.316 mol) of triethylamine and 1 g of 4-dimethylaminopyridine are dissolved in 750 ml of toluene, and 60 g (0.31 mol) of tosyl chloride in 450 ml of toluene are added dropwise. The mixture is stirred for two days at room temperature, water is added, and the aqueous phase is separated off and extracted with toluene. The toluene solutions are washed with 10% hydrochloric acid, dried over magnesium sulphate, concentrated, dissolved in ethyl acetate and filtered through silica gel. The filtrate is concentrated.

Yield: 125 g (91% of theory).

The thin-layer chromatogram shows a homogeneous compound.

d) trans-3-bromo-1-tosyl-4-(2-tosyloxyethoxy)-pyrrolidine

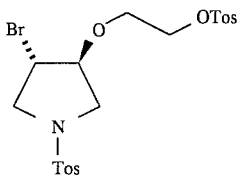

According to the same procedure as in Example 3c), trans-3-bromo-4-(2-hydroxyethoxy)-1-tosylpyrrolidine is reacted.

Yield: 100% of theory Melting point: 144° C. (from ethanol).

e) cis-8-benzoyl-5-benzyl-2-oxa-5,8-diazabicyclo[4.3.0]nonane

[Structure: cis bicyclic compound with O, N—Bzl, and N-benzoyl groups]

124 g (0.265 mol) of trans-1-benzoyl-3-bromo-4-(2-tosyloxyethoxy)-pyrrolidine are heated with 86 g (0.3 mol) of benzylamine in 1.5 l of xylene under reflux overnight. The salts of the benzylamine are filtered off with suction, and the filtrate is concentrated.

Crude yield: 91.2 g.

f) cis-5-benzyl-8-tosyl-2-oxa-5,8-diazabicyclo[4.3.0]nonane

[Structure: cis bicyclic compound with O, N—Bzl, and N-Tos groups]

According to the same procedure as in Example 3e), trans-3-bromo-1-tosyl-4-(2-tosyloxyethoxy)-pyrrolidine is reacted.

Yield: 84% of theory Melting point: 122° C. (from solvent naphtha/butanol 1:1)

g) cis-5-benzyl-2-oxa-5,8-diazabicyclo[4.3.0]nonane

[Structure: cis bicyclic compound with O, N—Bzl, and N-H groups]

Process A 91 g (0.265 mol) of cis-8-benzoyl-5-benzyl-2-oxa-5,8-diazabicyclo[4.3.0]nonane with 200 ml of concentrated hydrochloric acid and 140 ml of water are heated under reflux overnight. After cooling, the benzoic acid is filtered off with suction, the solution is reduced to half the volume and made alkaline with potassium carbonate and extracted with chloroform, the extract is dried over potassium carbonate, concentrated and distilled.

Yield: 30.7 g (48.8% of theory), Boiling point: 134° to 142° C./0.6 mbar, Content according to GC: 92%.

Process B 575 g (1.54 mol) of cis-5-benzyl-8-tosyl-2-oxa-5,8-diazabicyclo[4.3.0]nonane are dissolved in 1.5 l of 33% HBr in acetic acid, 310 g of phenol are added, and the mixture is stirred overnight at room temperature. 2 l of diisopropyl ether are added, and the dihydrobromide is filtered off with suction, washed with 0.5 l of diisopropyl ether and dried in air.

Yield: 505 g (86% of theory).

The dihydrobromide is dissolved in 1 l of water, and 45% sodium hydroxide solution is added until there is a strongly alkaline reaction. The organic phase is separated off, the aqueous phase is extracted three times with a total of 1 l of tert-butyl methyl ether and once with 300 ml of butanol. The organic solutions are dried over $K_2CO_3$ and concentrated, and the residue is distilled.

Yield: 273 g (81% of theory) Boiling point: 130° C./0.07 mbar.

EXAMPLE 4

Enantiomer resolution of cis-5-benzyl-2-oxa-5,8-diazabicyclo [4.3.0]nonane 150.1 g (1 mol) of D(−)-tartaric acid are introduced at 60° to 65° C. into 700 ml of methanol, and 218.3 g (1 mol) of cis-5-benzyl-2-oxa-5,8-diazabicyclo[4.3.0]nonane are added dropwise as a solution in 300 ml of methanol. The solution is allowed to cool slowly to approximately 49° C. until it becomes turbid, seeded with crystals of 1R,6S-5-benzyl-2-oxa-5,8-diazabicyclo[4.3.0]nonane D-tartrate obtained in a preliminary experiment, stirred for another 30 minutes at this temperature to produce crystallisation nuclei, and then slowly cooled to 0° to 3° C. After filtering with suction, the filtrate is washed with a mixture, cooled to 0° C., of 200 ml of ethanol and 100 ml of methanol, and then 3 times with 300 ml of ethanol each time, and the product is subsequently dried in air.

Yield: 160.3 g of 1R,6S-5-benzyl-2-oxa-5,8-diazabicyclo-[4.3.0]nonane tartrate (87% of theory) Melting point: 174.5° to 176.5° C. ee>97% (according to derivatisation with 1-phenylethyl isocyanate and evaluation by HPLC) $[\alpha]_D^{23}=+24.0°$ (c=1, methanol)

156.9 g of the 1st crop of crystals are recrystallised from 1500 ml of methanol.

Yield: 140.0 g (89% recovered) Melting point: 176° to 177° C. $[\alpha]_D^{23}=+25.2°$ (c=1, methanol)

The methanolic mother liquor of the 1st crystallisation is concentrated in a rotary evaporator. The syrupy residue (236 g) is dissolved in 500 ml of water, adjusted to pH 12 to 13 with 250 ml of 6N sodium hydroxide solution, and extracted three times with 350 ml of toluene each time, the extract is dried over sodium carbonate and concentrated under reduced pressure. The residue, 113.1 g of a brown oil which, according to examination by gas chromatography, contains 97% of cis- 5-benzyl-2-oxa-5,8-diazabicyclo[4.3.0]nonane, is used without further purification for preparing the 1S,6R enantiomer.

113.1 g (0.518 mol) of crude enriched 1S,6R-5-benzyl-2-oxa-5,8-diazabicyclo[4.3.0]nonane are dissolved in 155 ml of methanol and added dropwise to a boiling solution of 77.8 g (0.518 mol) of L(+)-tartaric acid in 363 ml of methanol. A mass of crystals gradually begins to form even during the dropwise addition. The mixture is stirred for another 1 hour at 60° C. and then slowly cooled to 0° C. over a period of 2 hours. The crystals are filtered off with suction and washed with a 2:1 mixture of ethanol and methanol cooled to 0° C., and subsequently washed 3 times with ethanol. They are then dried in air.

Yield: 145.5 g of 1S,6R-5-benzyl-2-oxa-5,8-diazabicyclo-[4.3.0]nonane L-tartrate (79% of theory) Melting point: 174.5° to 176.5° C. ee>97% (according to derivatisation with 1-phenylethyl isocyanate and evaluation by HPLC) $[\alpha]_D^{23}=-24.0°$ (c=1, methanol)

Liberation of the enantiomerically pure bases: 144 g (0.39 mol) of 1S,6R-5-benzyl-2-oxa-5,8-diazabicyclo[4.3.0]nonane tartrate are dissolved in 250 ml of water, and 175 ml (1.05 mol) of 6N sodium hydroxide solution are added. The deposited oil is taken up in 500 ml of toluene, the organic phase is separated off, and the aqueous phase is extracted 3 more times with 250 ml of toluene each time. The combined organic phases are dried over sodium carbonate, filtered and concentrated in a rotary evaporator. The residue is distilled over a 20 cm Vigreux column under high vacuum.

Yield: 81.6 g (96% of theory) of 1S,6R-5-benzyl-2-oxa-5,8-diazabicyclo[4.3.0]nonane Boiling point: 120° to 139° C./0.04 to 0.07 mbar Content: 100% as determined by gas chromatography Density: =1.113 g/ml $[\alpha]_D^{23}=-60.9°$ (undiluted) Distillation residue: 0.12 g In the same way, 76.0 g (93% of theory) of 1R,6S-5-benzyl-2-oxa-5,8-diazabicyclo[4.3.0]nonane are obtained from 139.2 g (0.376 mol) of 1R,6S-5-benzyl-2-oxa-5,8-diazabicyclo[4.3.0]nonane tartrate. $[\alpha]_D^{23}=+60.9°$ (undiluted)

The enantiomer resolution described for the cis-5-benzyl-2-oxa-5,8-diazabicyclo[4.3.0]nonane can also be performed analogously on trans-8-benzyl-2-oxa-5,8-diazabicyclo[4.3.0]nonane to give R,R- and S,S-8-benzyl-2-oxa-5,8-diazabicyclo[4.3.0]nonane.

EXAMPLE 5 a) 3S,4S-4-Allyloxy-3-hydroxypyrrolidine-1-carboxylic acid tert-butyl ester

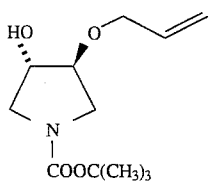

16.5 g (0.55 mol) of 80% NaH in 500 ml of absolute dioxane are introduced initially, and a solution prepared by dissolving 107.5 g (0.53 mol) of S,S-3,4-dihydroxypyrrolidine-1-carboxylic acid tert-butyl ester (German Offenlegungsschrift 3 403 194 of which U.S. Pat. No. 4,634,775 in an English language counterpart thereof) in hot absolute dioxane is added dropwise at 60° C. The mixture is stirred for one hour at 60° C., and 64 g (0.53 mol) of allyl bromide are then added dropwise. The mixture is then stirred for three hours at 60° C. It is concentrated, and the residue is dissolved in 200 ml of water and 600 ml of methanol. After extraction three times with 200 ml of pentane each time, the methanol is stripped off in a rotary evaporator, 200 ml of water are added as a diluent, and methylene chloride is used for extraction. The methylene chloride solution is dried over MgSO₄, concentrated and dissolved in tert-butyl methyl ether (200 ml). 9 g of starting material (44 mmol) crystallised from this solution. The ether solution is concentrated and distilled.

Yield: 83 g (80% of theory based on recovered starting material and diallyl ether) Boiling point: 149° C./0.7 mbar to 159° C./0.9 mbar.

The distillate contains 5% of starting material and 4% of diallyl ether.

The pentane extract gave 17 g of a mixture of 15% of the desired product and 84% of the diallyl ether. $[\alpha]_D^{23}=-10.5°$ (c=1, methanol).

b) 3S,4S-3-Hydroxy-4-(2-hydroxyethoxy)-pyrrolidine-1-carboxylic acid tert-butyl ester

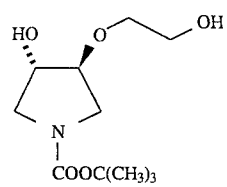

64 g (0.24 mol, 91%) of 3S,4S-4-allyloxy-3-hydroxypyrrolidine-1-carboxylic acid tert-butyl ester are dissolved in 250 ml of methanol, the solution is cooled to 0° C. and ozone is passed through until a wash bottle downstream charged with potassium iodide solution indicates the presence of ozone and thus that the reaction is complete. Residual ozone is flushed out by a stream of nitrogen, the ozonide produced is the then reduced at 0° C. with 18 g of sodium borohydride which is added in portions of 1 g. Subsequently, the mixture is stirred overnight at room temperature, the batch is concentrated and diluted with water, followed by the addition of 20 g of potassium carbonate and extraction five times with 100 ml of methylene chloride each. The organic solutions are dried over magnesium sulphate and concentrated.

Yield: 65.8 g (100% of theory). Content: 91% (determined by gas chromatography). $[\alpha]_D^{20}=-15°$ (c=0.97, methanol).

c) 3S,4S-3-Tosyloxy-4-(2-tosyloxyethoxy)-pyrrolidine-1-carboxylic acid tert-butyl ester

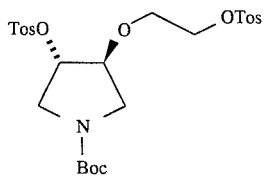

2.7 g (10 mmol, 91%) of 3S,4S-3-hydroxy-4-(2-hydroxyethoxy)-pyrrolidine-1-carboxylic acid tert-butyl ester in 30 ml of methylene chloride are introduced initially, followed by the addition of 6 ml of 45% sodium hydroxide and 0.1 g of benzyltriethylammonium chloride, and then the dropwise addition, with cooling, of a solution of 3.86 g (20 mmol) of tosyl chloride in 10 ml of methylene chloride. The mixture is then stirred for another hour at room temperature and poured into 20 ml of water, the organic phase is separated off, and the aqueous phase is extracted with methylene chloride. The organic phases are dried over magnesium sulphate and concentrated.

Yield: 5 g (90% of theory)

The product is uniform as determined by thin layer chromatography.

d) 1S,6R-5-Benzyl-2-oxa-5,8-diazabicyclo[4.3.0]nonane-8-carboxylic acid tert-butyl ester

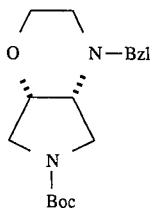

87 g (156 mmol) of 3S,4S-3-tosyloxy-4-(2-tosyloxyethoxy)-pyrrolidine-1-carboxylic acid tert-butyl ester are heated with 58 g (0.54 mol) of benzylamine in 1 l of xylene overnight under reflux. The mixture is cooled, precipitated benzylamine salts are filtered off with suction, and the residue is concentrated.

Yield: 43 g (58% of theory). Content: 67% (determined by gas chromatography).

e) 1S,6R-5-Benzyl-2-oxa-5,8-diazabicyclo[4.3.0]nonane

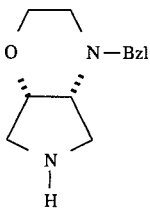

43 g (90 mmol) of 1S,6R-5-benzyl-2-oxa-5,8-diazabicyclo[4.3.0]nonane-8-carboxylic acid tert-butyl ester in 35 ml of concentrated hydrochloric acid and 35 ml of water are heated under reflux until the evolution of carbon dioxide ceases. The mixture is made alkaline with potassium carbonate and extracted with chloroform, the organic solutions are dried over $MgSO_4$ and concentrated, and two distillations are carried out with a 20 cm Vigreux column.

Yield: 11.1 g (55% of theory) Boiling point: 108° to 115° C./0.07 mbar $[\alpha]_D^{26}=-58.3°$ (undiluted).

EXAMPLE 6 a) 3R,4R-4-Allyloxy-3-hydroxypyrrolidine-1-carboxylic acid tert-butyl ester

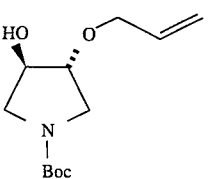

Reaction similar to Example 5a) from R,R-3,4-dihydroxypyrrolidine-1-carboxylic acid tert-butyl ester Boiling point: 145° C./0.1 mbar $[\alpha]_D^{23}=+9.5°$ (c=1.0, methanol) Content: 95% (determined by gas chromatography)

b) 3R,4R-3-Hydroxy-4-(2-hydroxyethoxy)-pyrrolidine-1-carboxylic acid tert-butyl ester

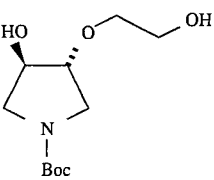

Reaction similar to Example 5b), using 3R,4R-4-allyloxy-3-hydroxypyrrolidine-1-carboxylic acid tert-butyl ester Yield: 99% of theory (0.175 molar batch) $[\alpha]_D^{20}=+16.5°$ (c=0.94, methanol)

c) 3R,4R-3-Tosyloxy-4-(2-tosyloxyethoxy)-pyrrolidine-1-carboxylic acid tert-butyl ester

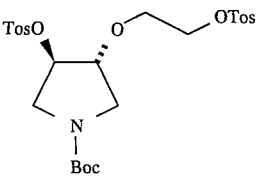

Reaction similar to Example 5c), using 3R,4R-3-hydroxy-4-(2-hydroxyethoxy)-pyrrolidine-1-carboxylic acid tert-butyl ester Yield: quantitative (0.11 molar batch).

d) 1R,6S-5-Benzyl-2-oxa-5,8-diazabicyclo[4.3.0]nonane-8-carboxylic acid tert-butyl ester

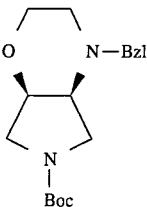

Reaction similar to Example 5d), using 3R,4R-3-tosyloxy- 4-(2-tosyloxyethoxy)-pyrrolidine-1-carboxylic acid tert-butyl ester Yield: 40% of theory (0.1 molar batch).

e) 1R,6S-5-Benzyl-2-oxa-5,8-diazabicyclo[4.3.0]nonane

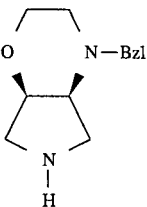

Reaction similar to Example 5e), using 1R,6S-5-benzyl-2-oxa-5,8-diazabicyclo[4.3.0]nonane-8-carboxylic acid tert-butyl ester Yield: 63% of theory (40 mmolar batch) Boiling point: 120° C./0.06 mbar Content: 95% (determined by gas chromatography). $[\alpha]_D^{28}=+58.5°$ (undiluted)

EXAMPLE 7 a) 1S,6R-2-Oxa-5,8-diazabicyclo[4.3.0]nonane dihydrochloride

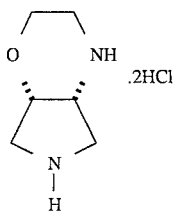

7.5 g (34.4 mmol), of 1S,6R-5-benzyl-2-oxa-5,8-diazabicyclo[4.3.0]nonane in 200 ml of ethanol with the addition of 7 ml of concentrated hydrochloric acid are hydrogenated using 1 g of palladium on activated carbon (10% Pd) at 100° C. and 100 bar. The catalyst is filtered off with suction and washed several times with water. The aqueous filtrate is concentrated, whereupon the residue crystallises. The crystals are thoroughly triturated with ethanol, filtered off with suction and dried in air.

Yield: 4.6 g (66.5% of theory) Melting point: 233° to 235° C.

b) 1S,6R-2-Oxa-5,8-diazabicyclo[4.3.0]nonane 59 g (0.27 mol) of 1S,6R-5-benzyl-2-oxa-5,8-diazabicyclo[4.3.0]nonane in 500 ml of ethanol are hydrogenated using 5 g of palladium on activated carbon (10% Pd) at 120° C. and 120 bar. The catalyst is filtered off with suction, the filtrate is concentrated and the residue is distilled.

Yield: 32.9 g (95% of theory) Boiling point: 65° C./0.03 mbar $[\alpha]_D^{28}$: +8.2° (undiluted).

Determination of the ee value using the Mosher reagent:

0.1 mmol of the amine is dissolved in 1.5 ml of toluene, 0.3 ml of 1N sodium hydroxide, 0.3 ml of water and 0.25 ml of a 1N solution of 3,3,3-trifluoro-2-methoxy-2-phenylpropanoyl chloride (Mosher reagent) in toluene are added, and the mixture is stirred for 30 minutes at room temperature. The toluene solution is removed by pipette and used directly for analysis by gas chromatography. The gas chromatogram shows only one detectable enantiomer (ee≧99.5%), while the racemate shows two baseline separated peaks for the Mosher derivatives of the two enantiomers.

EXAMPLE 8 a) 1R,6S-2-Oxa-5,8-diazabicyclo[4.3.0]nonane dihydrochloride

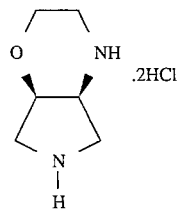

The reaction is carried out similarly to Example 7a), using 1R,6S-5-benzyl-oxa-5,8-diazabicyclo[4.3.0]nonane.

Yield: 77% of theory (23.8 molar batch Melting point: 230° to 232° C.

b) 1R,6S-2-Oxa-5,8-diazabicyclo[4.3.0]nonane

The reaction is carried out similarly to Example 7b), using 1R,6S-5-benzyl-2-oxa-5,8-diazabicyclo[4.3.0]nonane.

Yield: 93.3% of theory (1.58 molar batch) Boiling point: 63° to 65° C./0.03 mbar $[\alpha]_D^{23}$:−8.4° (undiluted) ee value: ≧99.5% (by derivatisation using Mosher reagent).

1R,6R- and 1S,6S-2-oxa-5,8-diazabicyclo[4.3.0]-nonane can be obtained similarly.

EXAMPLE 9 a) 1R,6S-5-(1R-Phenylethyl)-8-tosyl-2-oxa-5,8-diazabicyclo[4.3.0]nonane

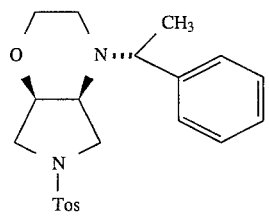

101.8 g (0.196 mol) of trans-3-bromo-1-tosyl-4-(2-tosyloxyethoxy)-pyrrolidine and 72 g (0.584 mol) of R-(+)-1-phenylethylamine in 900 ml of xylene are heated under reflux overnight. The cooled solution is washed with 2N sodium hydroxide solution and dried over potassium carbonate, the drying agent is removed and the solution is concentrated. Upon cooling, crystals separate from the residue and were filtered off with suction and recrystallised from a mixture of 750 ml of solvent naphtha and 200 ml of n-butanol.

Yield: 15 g (39.6% of theory of optically pure material) Melting point: 188° C. $[\alpha]_D^{28}$: +103.7° (c=1, CHCl$_3$).

b) 1R,6S-8-Tosyl-2-oxa-5,8-diazabicyclo[4.3.0]nonane

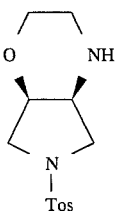

13 g (33.6 mmol) of 1R,6S-5-(1R-phenylethyl)-8-tosyl-2-oxa-5,8-diazabicyclo[4.3.0]nonane in 200 ml of ethanol are hydrogenated, using 2.5 g of palladium on activated carbon (10% Pd) at 100° C. and 100 bar. The catalyst is filtered off with suction, the filtrate is concentrated, and the product recrystallised from 30 ml of toluene.

Yield: 7.5 g (79% of theory) Melting point: 160° to 161° C. $[\alpha]_D^{23}$: +17.5° (c=1.21, CHCl$_3$).

c) 1R,6S-2-Oxa-5,8-diazabicyclo[4.3.0]nonane dihydrobromide

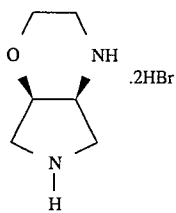

7 g (24.8 mmol) of 1R,6S-8-tosyl-2-oxa-5,8-diazabicyclo[4.3.0]nonane are dissolved in 25 ml of 33% strength hydrogen bromide solution in acetic acid, 5 g of phenol are added, and the mixture is stirred overnight at room temperature. After dilution with diisopropyl ether the salt which has crystallised is filtered off with suction and dried in air.

Yield: 5.5 g

Derivatisation with Mosher reagent, and analysis by gas chromatography (see Example 5) shows only one detectable enantiomer (ee $\geq$99.5%).

REFERENCE EXAMPLE 1

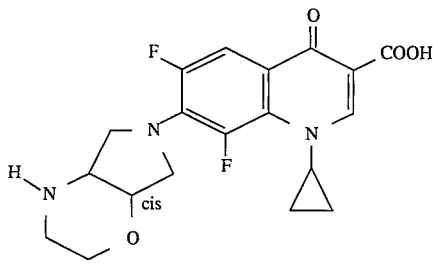

A. 1-Cyclopropyl-6,8-difluoro-1,4-dihydro-7-(cis-2-oxa-5,8-diazabicyclo[4.3.0]non-8-yl)-4-oxo-3-quinolinecarboxylic acid:

1.43 g (5 mmol) of 1-cyclopropyl-6,7,8-trifluoro- 1,4-dihydro-4-oxo-3-quinolinecarboxylic acid in a mixture of 15 ml of acetonitrile and 75 ml of dimethylformamide in the presence of 0.67 g (6 mmol) of 1,4-diazabicyclo[2.2.2]octane are heated under reflux for 1 hour with 0.74 g (5.4 mmol) of 93% cis-2-oxa-5,8-diazabicyclo[4.3.0]nonane. The suspension is concentrated, the residue is stirred with water, and the precipitate is filtered off with suction and dried in vacuo at 80° C.

Yield: 1.67 g (85.4% of theory), Melting point: 210°–212° C. (with decomposition).

B. 1-Cycloptopyl-6,8-difluoro-1,4-dihydro-7-(cis-2-oxa-5,8-diazabicyclo[4.3.0]non-8-yl)-4-oxo-3-quinolinecarboxylic acid hydrochloride:

1.6 g (4 mmol) of the product from step A are dissolved in 120 ml of half-concentrated hydrochloric acid at 60° C., the solution is concentrated, the residue is stirred with ethanol, and the precipitate is filtered off with suction and dried at 90° C. in vacuo.

Yield: 1.57 g, Melting point: 300°–303° C. (with decomposition), Content (HPLC): 97%.

C. Similarly to Reference Example 1A, using 1R,6S-2-oxa-5,8-diazabicyclo[4.3.0]nonane, 1-cyclopropyl-6,8-difluoro-1,4-dihydro- 7-(1R,6S-2-oxa-5,8-diazabicyclo[4.3.0]non-8-yl)-4-oxo-3-quinolinecarboxylic acid of melting point 204° to 206° C. (with decomposition) is obtained.

D. Similarly to Reference Example 1B, using the betaine from Reference Example 1C, 1-cyclopropyl-6,8-difluoro-1,4-dihydro- 7-(1R,6S-2-oxa-5,8-diazabicyclo[4.3.0]non-8-yl)-4-oxo-3-quinolinecarboxylic acid hydrochloride of melting point 324° to 325° C. (with decomposition) is obtained. $[\alpha]_D^{24}$: –241° (c=0.59, $H_2O$).

E. Similarly to Reference Example 1A, using 1S,6R-2-oxa-5,8-diazabicyclo[4.3.0]nonane, 1-cyclopropyl-6,8-difluoro- 1,4-dihydro-7-(1S,6R-2-oxa-5,8-diazabicyclo[4.3.0] non-8-yl)-4-oxo-3-quinolinecarboxylic acid of melting point 204° to 206° C. (with decomposition) is obtained. $[\alpha]_D^{25}$: +248° (c=0.57, DMF).

F. Similarly to Reference Example 1B, using the betaine from Reference Example 1E, 1-cyclopropyl-6,8-difluoro-1,4-dihydro- 7-(1S,6R-2-oxa-5,8-diazabicyclo[4.3.0]non-8-yl)-4-oxo-3-quinolinecarboxylic acid hydrochloride of melting point 323° C. (with decomposition) is obtained. $[\alpha]_D^{26}$: +238° (c=0.5, $H_2O$).

REFERENCE EXAMPLE 2

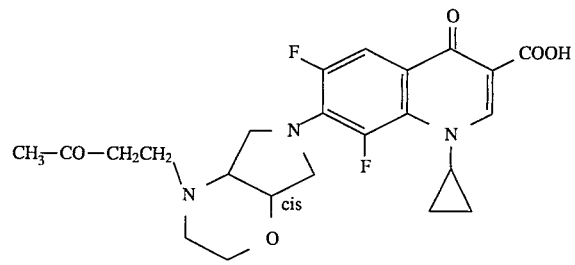

1.56 g (4 mmol) of the product from Reference Example 1A are heated with 1.8 g (25.6 mmol) of methyl vinyl ketone in 50 ml of ethanol for 3 hours under reflux. The suspension is concentrated at 70° C./12 mbar, and the residue is mixed with water and recrystallised from glycol monomethyl ether.

Yield: 1.33 g (72% of theory) of 1-cyclopropyl-6,8-difluoro-1,4-dihydro- 4-oxo-7-(cis-5-[3-oxo-1-butyl]-2-oxa-5,8-diazabicyclo[4.3.0]non-8-yl)-3-quinolinecarboxylic acid, melting point: 188°–189° C. (with decomposition).

What is claimed is:

1. A process for the preparation of an enantiomerically pure compound of the formula (I)

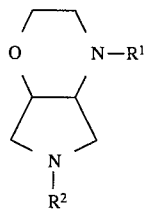

in which $R^1$ represents H, $C_1$–$C_3$-alkyl, phenyl, benzyl, 1-phenylethyl, $C_1$–$C_3$-alkanoyl, or $C_1$–$C_4$-alkoxycarbonyl, and $R^2$ represents H, benzyl, $C_1$–$C_5$-alkanoyl, benzoyl which is optionally mono- or disubstituted by halogen or $C_1$–$C_4$-alkyl, $C_1$–$C_4$-alkoxycarbonyl, methanesulphonyl, benzenesulphonyl or toluenesulphonyl, which comprises reacting a S,S- or R,R-dihydropyrrolidine derivative of the formula (VIIIa) or (VIIIb)

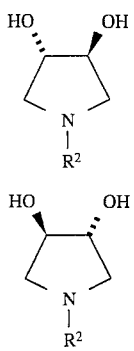
(VIIIa)

(VIIIb)

in which $R^2$ is defined above except that it is not hydrogen, with allyl bromide or allyl chloride in the presence of a base to give a compound of the formula (IXa) or (IXb)

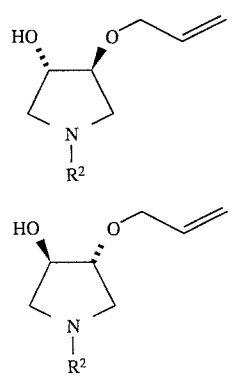
(IXa)

(IXb)

breaking down the compound (IXa) or (IXb) by ozonolysis and subsequent reduction, into a compound of the formula (Xa) or (Xb) respectively,

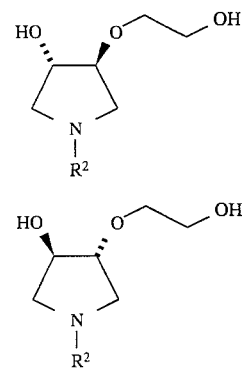
(Xa)

(Xb)

which, compounds (Xa) or (Xb) are reacted with a sulphonyl chloride, $R^3$—$SO_2Cl$, to give a sulphonic acid ester of the formula (XIa) or (XIb) respectively,

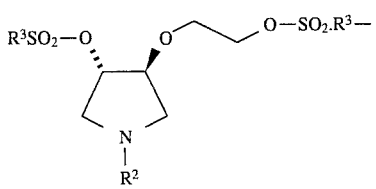
(XIa)

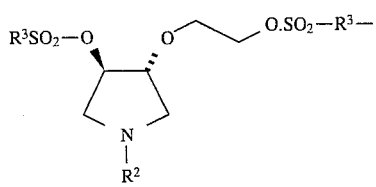
(XIb)

$R^3$ is methyl, phenyl or methylphenyl, and compounds (XIa) or (XIb) are reacted with a amine of the formula (IV), $$R^4—NH_2 \qquad (IV)$$

wherein $R^4$ is hydrogen, $C_1$–$C_3$-alkyl, phenyl, benzyl or 1-phenylethyl to give a compound of the formula (Va) or (Vb) respectively

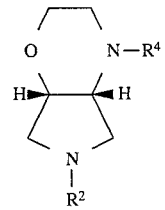
(Va)

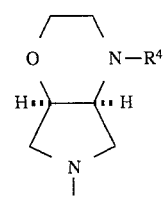
(Vb)

optionally removing the protective radicals $R^2$ and/or $R^4$, and reacting the secondary nitrogen atoms of the compound thus obtained again with compounds $R^1$—X and $R^2$—X, wherein X is a leaving group, and isolating one enantiomerically pure compound of formula I.

2. A process according to claim 1, wherein $R^1$ represents H, methyl, benzyl, 1-phenylethyl, acetyl, ethoxycarbonyl or t-butoxycarbonyl, and $R^2$ represents H, benzyl, acetyl, benzoyl, ethoxycarbonyl, t-butoxycarbonyl, methanesulphonyl or p-toluenesulphonyl.

* * * * *